(12) United States Patent
Huang et al.

(10) Patent No.: US 7,383,730 B2
(45) Date of Patent: Jun. 10, 2008

(54) METHODS FOR DETERMINING VELOCITY OF A STRESS WAVE WITHIN A MATERIAL AND HOMOGENEITY OF PROPERTIES WITHIN THE MATERIAL

(75) Inventors: Chih-Lin Huang, Bellevue, WA (US); Stanley L. Floyd, Enumclaw, WA (US)

(73) Assignee: Weyerhaeuser Company, Federal Way, WA (US)

( * ) Notice: Subject to any disclaimer, the term of this patent is extended or adjusted under 35 U.S.C. 154(b) by 307 days.

(21) Appl. No.: 11/096,763

(22) Filed: Mar. 31, 2005

(65) Prior Publication Data

US 2006/0219012 A1    Oct. 5, 2006

(51) Int. Cl.
*G01N 29/12* (2006.01)

(52) U.S. Cl. .......................................... 73/597; 73/602
(58) Field of Classification Search ............... 73/579
See application file for complete search history.

(56) References Cited

U.S. PATENT DOCUMENTS

| | | | | |
|---|---|---|---|---|
| 5,024,091 A | * | 6/1991 | Pellerin et al. | 73/597 |
| 5,339,691 A | * | 8/1994 | Smith et al. | 73/597 |
| 6,026,689 A | * | 2/2000 | Snyder et al. | 73/602 |
| 6,715,337 B2 | * | 4/2004 | Huang et al. | 73/12.12 |

* cited by examiner

*Primary Examiner*—Hezron E. Williams
*Assistant Examiner*—Rose M Miller

(57) ABSTRACT

Methods for evaluating properties of a material are provided. In a first method, the velocity of a stress or sound wave is calculated by measuring the time of flight of the stress/sound wave induced into the material. The resonance of the material is also measured after the wood product is contacted. A separate velocity of the sound wave within the material is calculated using the resonance measurements. A comparison of the individual velocities provides an indication of the homogeneity of properties of the material. The properties may be, for example, stiffness, strength, various gradients or the like. In a second method of the present invention, the velocity calculated using the time of flight method may be used as a guide in determining a fundamental frequency for the stress wave within a material and resultant velocity. The material may be, for example, wood, metal, plastic or the like.

15 Claims, 7 Drawing Sheets

METHODS FOR DETERMINING VELOCITY OF A STRESS WAVE WITHIN A MATERIAL AND HOMOGENEITY OF PROPERTIES WITHIN THE MATERIAL

FIELD OF THE INVENTION

This invention relates generally to the use of time of flight and resonance frequency of propagating acoustic waves within a material to determine the properties of the material, including warp potential, stiffness and other characteristics. The material may be wood, metal, plastic or similar substance

BACKGROUND OF THE INVENTION

It is generally known that acoustic measurement can be used to determine properties of a material, such as, a wood product. These properties may include, for example, stiffness, strength, elasticity and other characteristics. In some embodiments, in which properties of a wood product are being ascertained, a stress wave is induced into the wood product. Next, a measurement is taken with respect to the time in which the stress wave travels from a first end to a second end of the wood product. From this time interval, a velocity of the stress wave can be determined via the equation:

$$v=d/t$$

Where "v" is velocity of the stress wave; "d" is the distance traveled by the stress wave; and "t" is the time period of travel. This method of determining velocity is commonly referred to as a "time-of-flight" method. The velocity can, for example, be correlated to a modulus of elasticity for the wood product, which is an indicator of the stiffness of the wood product.

Another method for determining properties of a material is through the use of resonance frequency. In this method, the material may be contacted, or struck, to induce a wave within the material. The different frequencies, or harmonics, at which the material resonates based on the induced wave may be measured. Higher order harmonics may be used to discern a fundamental frequency for resonation. Using the obtained fundamental frequency, the velocity of the wave can be determined via the equation:

$$v=2fL$$

where "v" is velocity of the stress wave; "f" is the fundamental frequency; and "L" is the length of the material.

This velocity may also provide information as to the stiffness or other characteristics of the material. Use of resonance frequency is well known when discerning properties of, for example, wood products.

However, many properties of materials, such as, for example, wood products, are not homogeneous throughout the product. Time-of-flight measurement tends to estimate the properties of the high stiffness path within a wood product; whereas resonance frequency measurement tends to estimate the average properties within that product. However, many wood products have imperfections such as knots or other structural defects. These defects can significantly alter the data measured via time of flight measurements and/or resonance frequency measurements as well as the overall findings regarding wood product properties.

In an example, FIG. 1 shows typical waveforms obtained from start and stop sensors used to measure acoustic velocity in wood by the time-of-flight technique. With this technique, it can be difficult to determine the exact time of arrival of the acoustic energy at the downstream (stop) sensor. The precise arrival time should be the instant when the acoustic energy begins to appear at the detector, thereby corresponding to the point when the detector output begins to rise. Unfortunately, most methods of detecting this leading edge are very sensitive to noise. Another technique commonly used to establish time of arrival is to locate the point where peak amplitude is reached. In the example shown in FIG. 1, this time-of-arrival ambiguity results in 20% uncertainty in the estimate of acoustic velocity. This data was taken on an 8 ft pine 2×4 using a FAKOPP® device, with start and stop sensors placed 7.5 feet apart.

FIG. 2 illustrates a typical output from an accelerometer attached to the same piece of lumber. The display shows the waveforms that are resonating within the lumber 2-5 milliseconds after a stress wave is induced. The data was taken from the same test used to generate FIG. 1. FIG. 3 is a display of the Fourier transform of the data shown in FIG. 2. This transform plot shows that the lumber piece is resonating at several frequencies. In this case, there is significant energy at 610 Hz, 1099 Hz, 1343 Hz, 2076 Hz, and 3541 Hz. These frequencies correspond to acoustic velocity estimates (ft/sec) of 9760, 16485, 21488, 33216, and 56656 respectively. It can be difficult to determine which of these velocity estimates represents the compression wave of interest. In this example, both the 9760 ft/sec and the 16,485 ft/sec estimates fall within the range of legitimate stress wave velocities normally associates with dry lumber.

A need, therefore, exists for a method for using both time of flight and resonance frequency measurements to provide greater accuracy and/or precision when determining a velocity of a wave within a material as well as to determine properties of the material.

SUMMARY OF THE INVENTION

The present invention provides methods for using time of flight and resonance frequency of propagating waves within a material to determine a velocity of a wave within a material and various properties of the material, such as, for example, stiffness, strength, homogeneity of properties and other characteristics. The material may be, for example, wood, wood composite, metal, metal alloy, ceramic, ceramic alloy, plastic, rubber, polymer, or the like. In an embodiment, the material is wood, such as in a wood product (i.e. log, board, cant, lumber, engineered wood product, plywood, oriented strand board, medium density fiberboard, particle board, etc). A first apparatus and/or system may contact the wood product which may be any type of wood product, such as, for example, a log, board, other type of lumber, engineered product, panel, or the like. This contact may induce a stress wave which may propagate through the wood product. The stress wave may travel from, for example, a first end of the wood product to a second end. The first apparatus and/or system may then measure a pulse created at the first end as well as the second end. In an embodiment, the first apparatus and/or system may measure a pulse at the first end and subsequently measure a pulse at the first end after the wave moves to second end and returns, or echoes, to the first end.

A second apparatus and/or system may be positioned adjacent to an end of the wood product. The second apparatus and/or system may measure the resonance of the wood product after it has been contacted. The measurements may be subject to an algorithm, such as a Fast Fourier Transform, to determine a fundamental frequency. Often the fundamental frequency is difficult to discern when examining FFT plots or measurements due to erratic peaks. In cases such as these, a time of flight calculation of velocity may be used as a guide when examining the FFT plot to determine the fundamental frequency.

In an example, two or more peak values may be provided after the resonance measurements are subject to a Fast Fourier Transform. These peaks may be considered candidate peaks. Each candidate peak correlates to a possible value for a velocity of the stress wave. Having determined a velocity of the stress wave based on the time of flight method, the most accurate peak may be selected by determining which peak value correlates to a velocity which is closest to the velocity determined via the time of flight method.

The fundamental frequency may be used to determine a velocity of a sound wave within the wood product. A value for the velocity of sound within the wood product may also be calculated based on the time of flight of the wave induced by the first apparatus and/or system. These values may be compared to determine homogeneity of properties within the wood product. For example, the velocity of sound calculated based on the measured time of flight may represent the velocity of sound along an outer area of the wood product which may be an area of higher stiffness. The velocity calculated via determination of the fundamental frequency may represent an average velocity throughout the wood product. It is hypothesized that, the closer the proximity of these values, the more homogeneous the wood product. It is further hypothesized that the proximity may be an indication of warp potential whereby closer proximity may indicate greater warp potential in younger trees and lesser warp potential in older trees. Further, it is contemplated that the above-described techniques may be utilized on other types of materials, including those listed above.

In an embodiment, a method is provided for determining a velocity of a stress wave within a material based on resonance measurements. The method comprises the steps of: inducing the stress wave into the material at a time $t_1$; measuring a first amplitude created at the time $t_1$; measuring a second amplitude at a time $t_2$ caused by travel of the stress wave through the material; measuring a distance traveled by the stress wave within the material in a period of time between the time $t_2$ and the time $t_1$; determining a first velocity of the stress wave by dividing the distance traveled by the stress wave by the period of time between the time $t_2$ and the time $t_1$; obtaining resonance measurements of the material after the time $t_1$; subjecting the resonance measurements to a Fast Fourier Transform algorithm to provide a plurality of candidate values for a second velocity of the stress wave, the second velocity being a velocity of the stress wave based on resonance measurements; and selecting a most accurate candidate value from the plurality of candidate values based on its proximity to the first velocity wherein the most accurate candidate value is considered the second velocity.

It is, therefore, an advantage of the present invention to provide a method for using time of flight and resonance frequency of propagating waves within a material to determine velocity of a stress wave within the material as well as various properties of the material.

Additional features and advantages of the present invention are described in, and will be apparent from, the detailed description of the present embodiments and from the drawings.

BRIEF DESCRIPTION OF THE DRAWINGS

The embodiments of the present invention are described in detail below with reference to the following drawings.

DETAILED DESCRIPTION OF THE INVENTION

The present invention relates to methods for using time of flight and resonance frequency of propagating waves within a material to determine velocity of a stress wave within the material as well as various properties of the material, such as, for example, stiffness, strength, homogeneity of properties and other characteristics. The material may be wood, wood composite, metal, metal alloy, ceramic, ceramic alloy, plastic, rubber, polymer, or the like. In an embodiment, the material is wood in the form of a wood product, such as a log, board, cant, lumber, engineered wood product, plywood, oriented strand board, medium density fiberboard, particle board, or the like. A first apparatus and/or system may contact the wood product and may induce a stress wave which may propagate through the wood product. Other known methods of stress wave inducement are also contemplated. The stress wave may travel from, for example, a first end of the wood product to a second end. The first apparatus and/or system may then measure a pulse created at the first end and/or the second end. A second apparatus and/or system may measure resonance of the wood product after impact. The resonance may be subject to an algorithm, such as, for example, a Fast Fourier Transform ("FFT"). The time of flight data measured by the first system may be used as a guide to determine the fundamental frequency, and harmonics, of the wave within the wood product. In addition, a comparison may be made between the velocity of sound based on the time of flight and the velocity of sound based on the fundamental frequency. This comparison may provide an indication of the homogeneity of the wood product.

Figure 7:
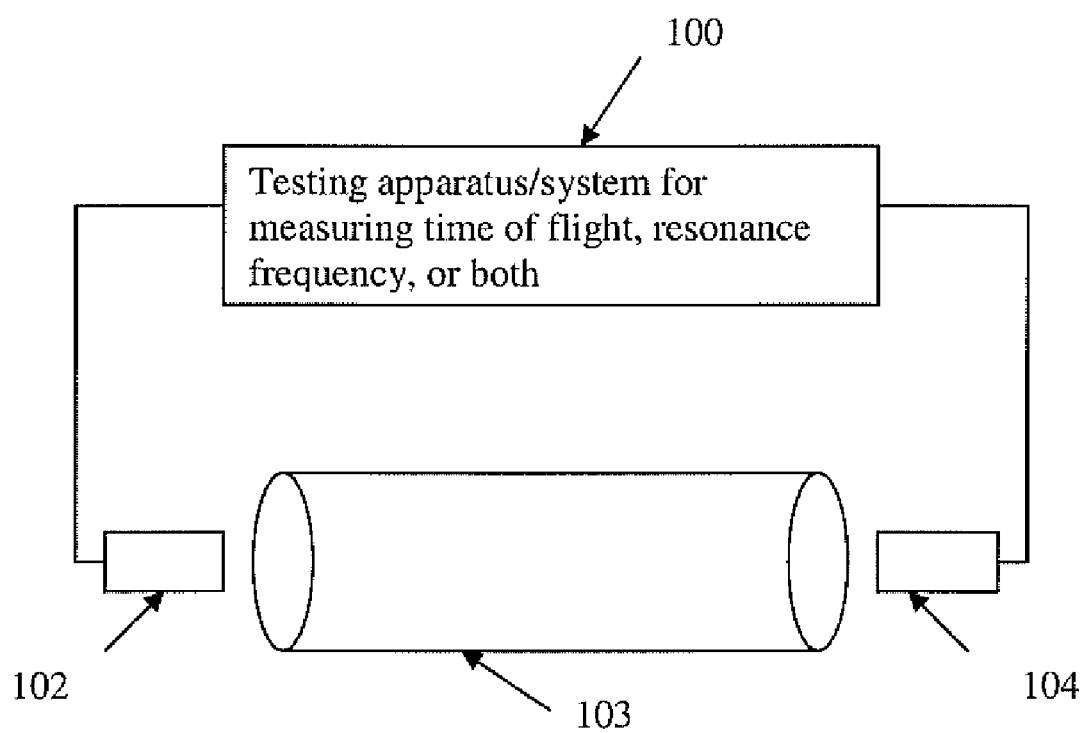
FIG. 7 is a diagram of a testing system or apparatus, and a material to be tested, in an embodiment of the present invention.
Figure 8:
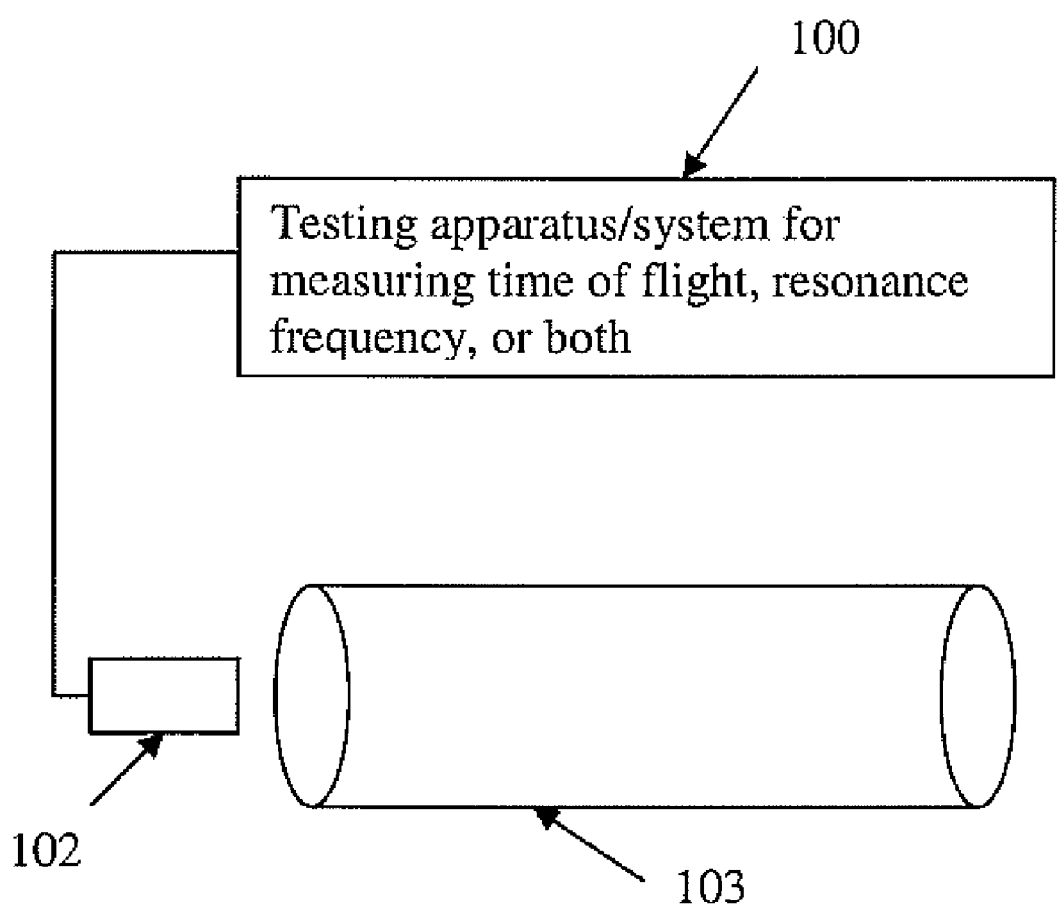
FIG. 8 is a diagram of a testing system or apparatus, and a material to be tested, in another embodiment of the present invention.

Different apparatuses and/or systems, known by those skilled in the art and illustrated in FIGS. 7 and 8, may be used to obtain the time of flight and the resonance frequency of a wood product. For time of flight measurements, single and double probe systems may be utilized. These apparatuses and/or systems 100 may calculate velocity using those equations previously described. In a single probe system, a probe, or transducer 102, is used to detect and record the waves which may reverberate back and forth within a log or a piece of lumber 103. This phenomenon may be characterized as "multiple passes" through the wood product.

In a two probe system, such as that demonstrated by a FAKOPP® system, a first probe 102 is placed at a first end of a wood product 103 and a second probe 104 is placed at a second end of the wood product. The first probe senses the initial pulse created by contact with the wood product, or other methods of stress wave inducement into the wood product. The second probe senses the pulse at the second end. This is commonly referred to as a "pitch-and-catch", or single pass, measurement. For standing trees, the pitch-and-catch method is more common due to the lack of a well-defined boundary of a standing tree.

Resonance may be measured by an apparatus and/or system, such as, for example, a WOODY®; Director HM200®, also known as a HITMAN®; or WOODSPEC®. The methods by which these systems generate and/or measure signals is known in the art. In an embodiment, the HITMAN® may be adjacent to the wood product, as it is struck or otherwise contacted, while also implementing FAKOPP® equipment. The HITMAN® may then measure the resonance of the propagating wave within the wood product.

In addition, it should be noted that any number of sensors may be implemented to obtain time of flight and/or resonance measurements. In an embodiment, the same sensor may be used to obtain both types of measurements. In other embodiments, multiple sensors may be used at different locations on the material wherein these sensors may or may not obtain both types of measurements.

Figure 1:
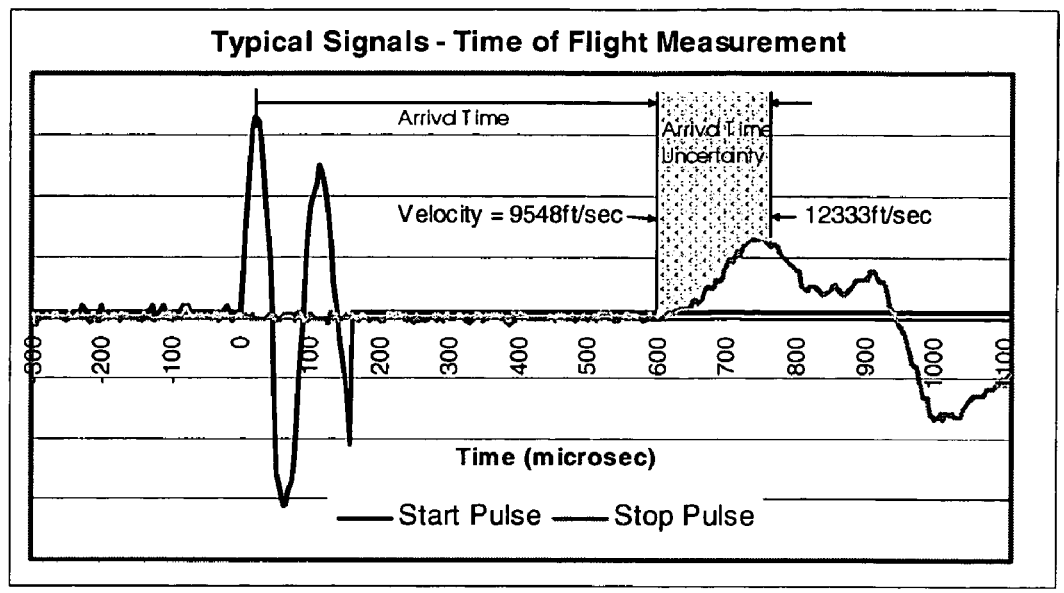
FIG. 1 is a plot of amplitude versus time for a stress wave induced into a wood product in an embodiment of the present invention.

Referring now to the drawings, FIG. 1 illustrates a plot of Amplitude versus Time for a signal created by the contacting of a wood product to induce a stress wave. In an embodiment, the time of flight may be calculated by identifying peak amplitudes. More specifically, a first peak amplitude is identified at the time $t_1$ a wood product is struck. A second peak amplitude is identified at a time $t_2$ when the stress wave arrives at the second sensor, or makes its return trip to the original sensor. The time between these peak amplitudes may provide a velocity of the stress wave. Namely, given the known distance (d) the stress wave must travel between measurements, and the difference in time between the readings by the sensor or sensors (i.e., $t_2-t_1$), the velocity (v) can be determined via the formula $v=d/(t_2-t_1)$.

In another embodiment, the velocity may be calculated via the use, or selection, of "threshold amplitudes". More specifically, these amplitudes or values may not be identified at peak amplitudes or initial portions of the peak amplitudes, but amplitudes proximate to the time the stress waves are initially sensed. A threshold value allows for reduction in measurement error due to noise created by wood product defects and/or variation in impact techniques. This threshold value may indicate a starting point for measurement of the stress wave. For example, if the time the wood product is contacted is $t_0$, then the threshold value may occur at a time $t_1$ after $t_0$ once a selected threshold value is reached by the amplitude. For example, an initial pulse may be created at a time $t_0$ by striking the wood product and may be measured by a first probe in a pitch and catch method. The initial pulse may be represented on a plot by the amplitude forming at the time $t_0$ and may reach the threshold value at the time $t_1$. This pulse may travel across the wood product and may eventually be measured by a second probe located, for example, at an opposite end of the wood product. This measurement is represented by the amplitude at a time $t_2$. The velocity of the wave within the wood product may then be determined using the distance between the first probe and the second probe and the difference in time between $t_2$ and $t_1$ in which the wave traveled between the first probe and the second probe.

Figure 2:
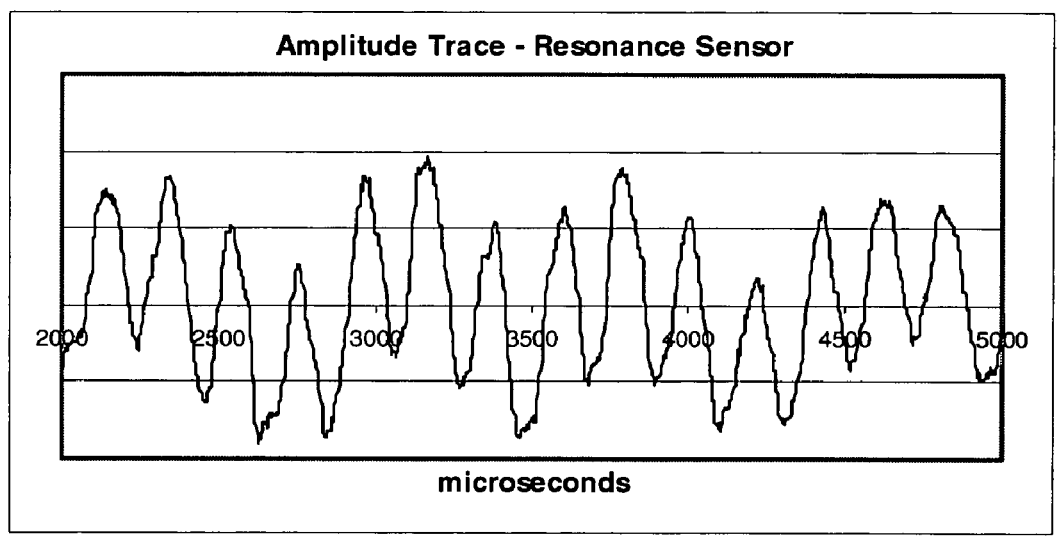
FIG. 2 is a time trace for the wood product.
Figure 3:
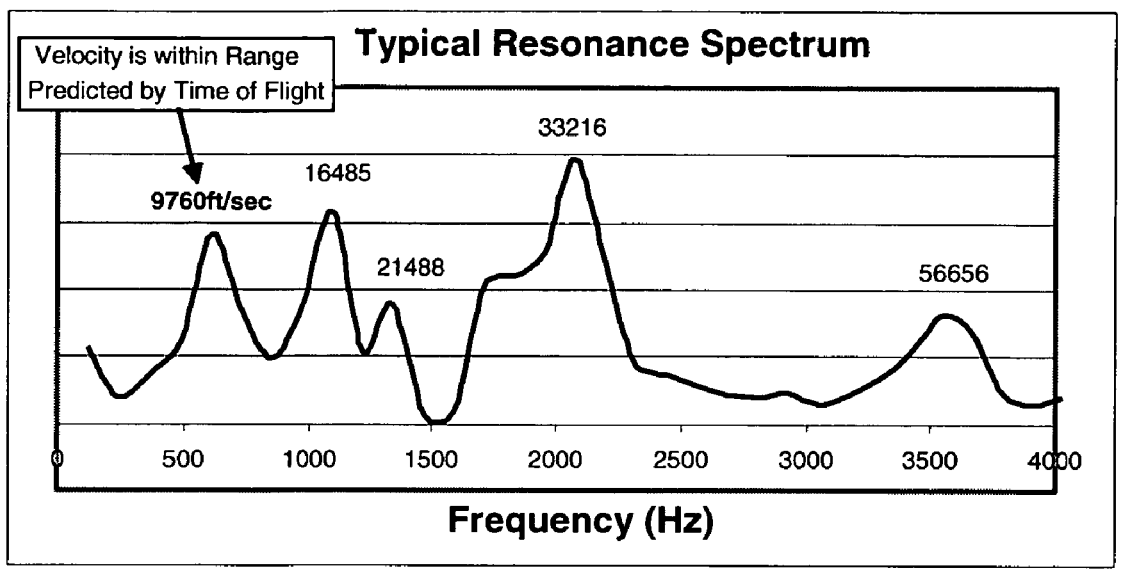
FIG. 3 is a frequency spectrum created by subjecting the time trace of FIG. 2 to an algorithm.
Figure 5:
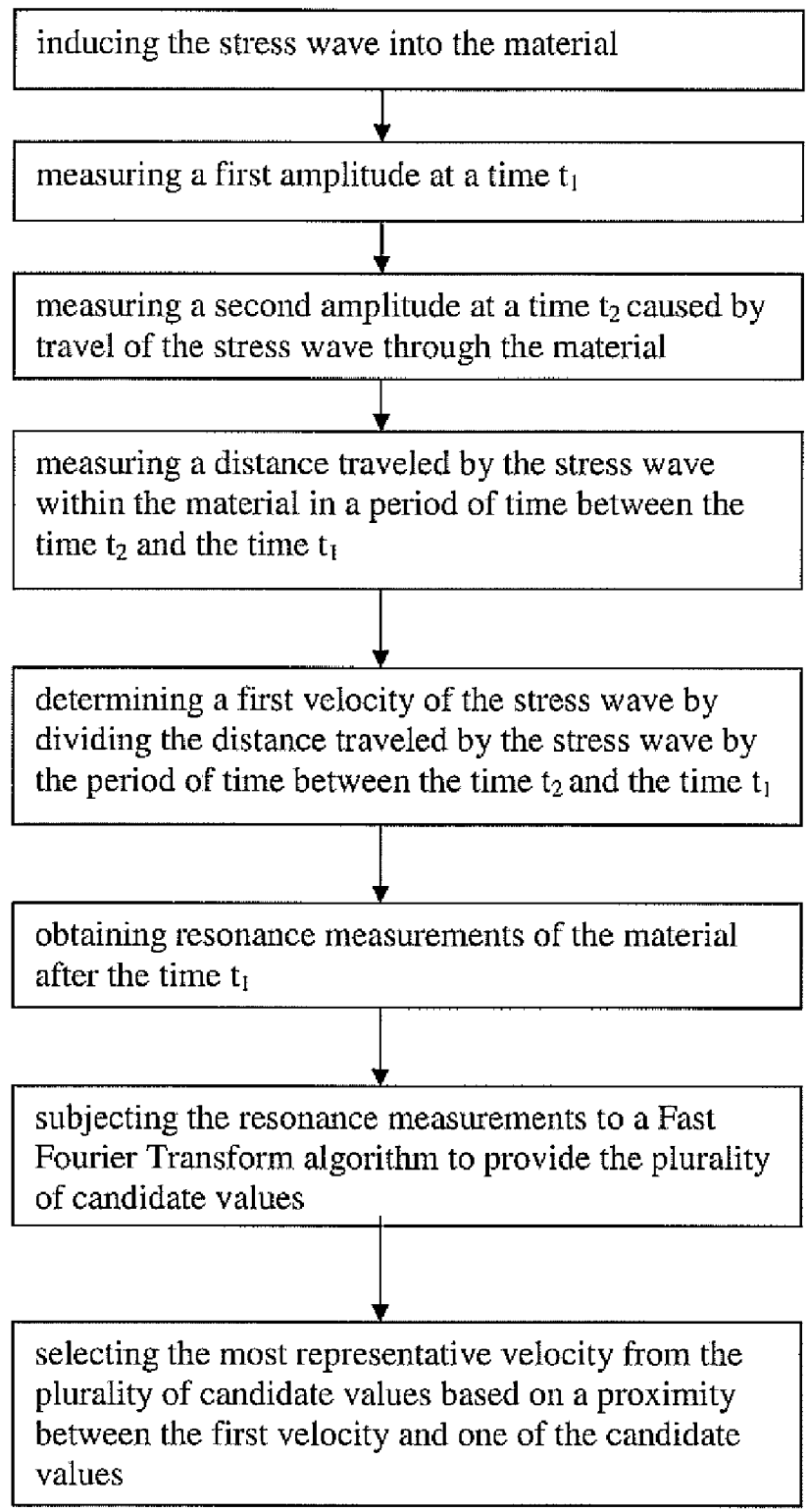
FIG. 5 is a flowchart of method for selecting a most representative velocity in an embodiment of the present invention.

The velocity calculated via the time of flight method may be used as a guide to identify the fundamental frequency at which the material resonates as illustrated in FIG. 5. To this end, resonance measurements may be obtained after a stress wave is induced within the material. These resonance measurements may then be subject to an algorithm, such as a Fast Fourier Transform analysis, known by those skilled in the art. This analysis provides one or more candidate peak values. To avoid misidentifying the fundamental frequency from others within a complex frequency spectrum, the fundamental frequency can be determined by the closest candidate peak, or via the peak with distinct shape which correlates to a velocity that is proximate to the velocity estimated by the time of flight method. More specifically, in the example previously provided in FIGS. 1-3, both the 9760 ft/sec and the 16,485 ft/sec estimates fall within the range of legitimate stress wave velocities normally associated with dry lumber. This ambiguity can be resolved by comparing the multiple resonance velocities with the velocity calculated via the time of flight method. By comparing the estimates of velocity from both techniques, it can be concluded that 9700 ft/sec is the correct average stress wave velocity for this piece of lumber.

Figure 6:
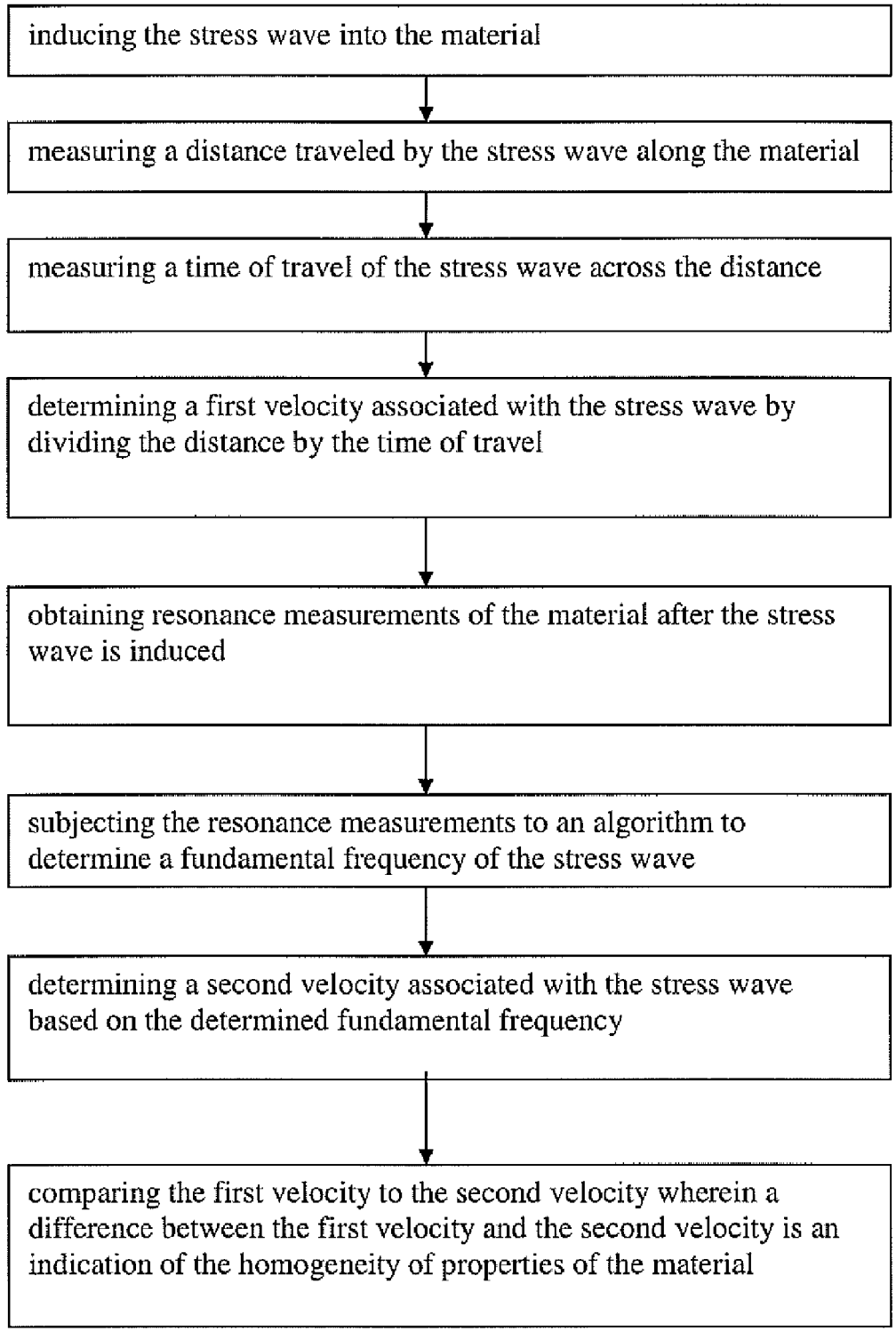
FIG. 6 is a flowchart of method for determining homogeneity of properties of a material in an embodiment of the present invention.

In an embodiment, a method is provided for evaluating a material. This method is illustrated in FIG. 6. In one step of the method, a velocity of a stress wave within the material is measured using the time of flight method. More specifically, the velocity is determined based on pulse measurements obtained after the material is struck or otherwise contacted to induce a stress wave. In another step of the method, a velocity of a sound wave is calculated after determining a fundamental frequency of a sound wave propagating through the material, i.e., using resonance frequency techniques. The method has an additional step of comparing the velocity calculated via time of flight measurements to the velocity calculated via resonance measurements. The comparison may enable an individual to characterize the homogeneity of properties of the material, such as, for example, a stiffness gradient for the material. This method may be applied to various materials, such as, for example, without limitation, wood, plastic, metal, ceramic, or the like. In the case of a wood product, such as, without limitation, a log, the velocity calculated via time of flight measurements may be considered a measurement of the velocity of a stress wave traveling along an outer portion of the wood product, since an outer portion of a wood product is usually the stiffest portion of the wood product. Exceptions to this principle occur if low moisture heartwood is present; in which case the acoustic wavefront created via time-of-flight methods may follow the heartwood path. The velocity calculated via resonance measurements may be considered an average of the velocity of the sound wave as it travels through all portions of the wood product. This may provide an indication of the average stiffness of the wood product. Accordingly, a comparison of the "time of flight" velocity and the "resonance" velocity may indicate differences in, for example, stiffness in a direction from the bark to the pith, respectively.

Figure 4:
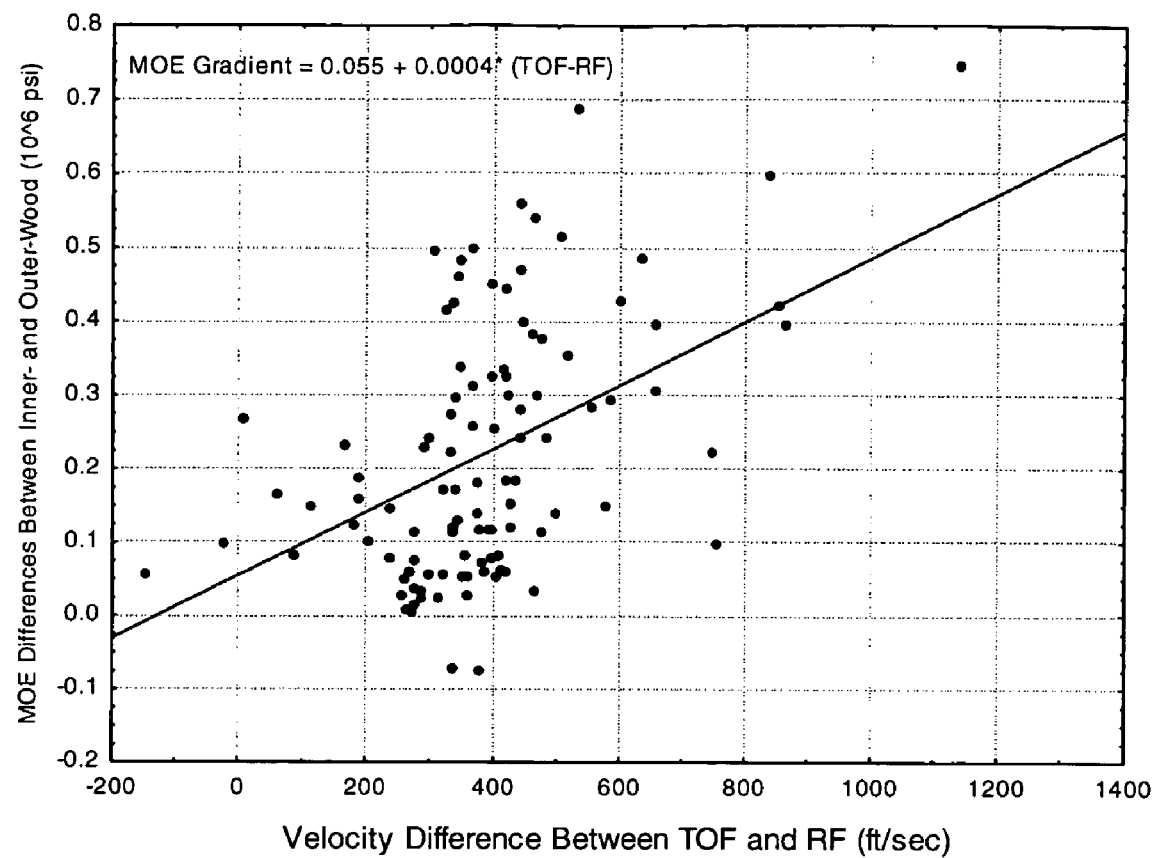
FIG. 4 is a plot of the difference between velocity determined via the use of time of flight measurement and velocity determined using resonance frequency methods and the correlation of the difference to a stiffness gradient of a wood product.

FIG. 4 illustrates a plot of the difference between velocity calculated using time of flight measurements ("$V_{TOF}$") and the velocity calculated using resonance measurements ("$V_R$") for a wood product. The plot may indicate that the difference between $V_{TOF}$ and $V_{RF}$ can be used to predict the modulus of elasticity gradient within the wood product. It is hypothesized that this type of comparison may be applied to other types of materials to obtain information regarding homogeneity of properties.

There are definite advantages to using time of flight and resonance frequency to calculate the velocity of a sound wave in a material, especially wood. For example, use of both methods reduces inaccuracies in velocity calculation due to limitations associated with each method. While resonance frequency measurements are affected by the geometry of, for example, a wood specimen, time of flight measurements are less affected. In other embodiments, such as those in which multiple-pass methods are used, the resonance measurements may be affected by phenomenon, such as, for example, wood product geometry or stacking effects when multiple wood products are placed adjacent to each other. Effects of dispersion and/or wave interference may also be considerable. Use of both methods may alleviate confusion which may occur when data is being gathered subject to the above conditions. In another example, it is understood that most resonance-based instruments rely on higher order harmonics. These high order harmonics can be highly confused when logs are stacked and/or have defects. A time of flight measurement may indicate which of these higher order harmonics to use in a resonance-based acoustic velocity determination.

While the embodiments of the invention have been illustrated and described, as noted above, many changes can be made without departing from the spirit and scope of the invention. Accordingly, the scope of the invention is not limited by the disclosure of the embodiments. Instead, the invention should be determined entirely by reference to the claims that follow.

What is claimed is:

1. A method for determining a most representative velocity of a stress wave within a material from a plurality of candidate values, the method comprising the steps of:
   inducing the stress wave into the material;
   measuring a first amplitude at a time $t_1$;
   measuring a second amplitude at a time $t_2$ caused by travel of the stress wave through the material;
   measuring a distance traveled by the stress wave within the material in a period of time between the time $t_2$ and the time $t_1$;
   determining a first velocity of the stress wave by dividing the distance traveled by the stress wave by the period of time between the time $t_2$ and the time $t_1$;
   obtaining resonance measurements of the material after the time $t_1$;
   subjecting the resonance measurements to a Fast Fourier Transform algorithm to provide the plurality of candidate values; and
   selecting the most representative velocity from the plurality of candidate values based on a proximity between the first velocity and one of the candidate values.

2. The method of claim 1 wherein the first amplitude and the second amplitude are measured by a single sensor.

3. The method of claim 1 wherein the first amplitude is measured by a first sensor and the second amplitude is measured by a second sensor wherein the first sensor and the second sensor are different.

4. The method of claim 1 further comprising the step of:
   comparing the first velocity to the most representative velocity to determine a homogeneity of properties within the material.

5. The method of claim 1 wherein the material is at least one of a wood, wood composite, metal, metal alloy, plastic, ceramic, ceramic alloy, rubber, and polymer.

6. A method for evaluating homogeneity of properties within a material, the method comprising the steps of:
   inducing a stress wave into the material;
   measuring a distance traveled by the stress wave along the material;
   measuring a time of travel of the stress wave across the distance;
   determining a first velocity associated with the stress wave by dividing the distance by the time of travel;
   obtaining resonance measurements of the material after the stress wave is induced;
   subjecting the resonance measurements to an algorithm to determine a fundamental frequency of the stress wave;
   determining a second velocity associated with the stress wave based on the determined fundamental frequency; and
   comparing the first velocity to the second velocity wherein a difference between the first velocity and the second velocity is an indication of the homogeneity of properties of the material.

7. The method of claim 6 wherein the time of travel is measured using a single transducer.

8. The method of claim 6 wherein the time of travel is measured using two transducers.

9. The method of claim 6 wherein the time of travel is measured by a first apparatus and the resonance is measured by a second apparatus wherein the first apparatus and the second apparatus are different.

10. The method of claim 6 wherein the time of travel and the resonance are measured by a single apparatus.

11. The method of claim 6 wherein the material is at least one of a wood, wood composite, metal, metal alloy, plastic, ceramic, ceramic alloy, rubber, and polymer.

12. A method for determining a most representative velocity of a wave within a wood product from a plurality of candidate values, the method comprising the steps of:
   inducing a stress wave into the wood product at a time $t_1$;
   measuring a first amplitude created at the time $t_1$;
   measuring a second amplitude at a time $t_2$ caused by travel of the stress wave through the wood product;
   measuring a distance traveled by the stress wave within the wood product in a period of time between the time $t_2$ and the time $t_1$;
   determining a first velocity of the stress wave by dividing the distance traveled by the stress wave by the period of time between the time $t_2$ and the time $t_1$;
   obtaining resonance measurements of the wood product after the time $t_1$;
   subjecting the resonance measurements to a Fast Fourier Transform algorithm to provide the plurality of candidate values; and
   selecting the most representative velocity from the plurality of candidate values based on a proximity between the first velocity and one of the candidate values.

13. The method of claim 12 wherein the wood product is at least one of a log, board, cant, lumber, engineered product, and panel.

14. The method of claim 12 wherein the stress wave is measured by one or more sensors.

15. The method of claim 12 further comprising the step of:
   comparing the first velocity to the most representative velocity to determine a homogeneity of properties within the wood product.

* * * * *